United States Patent [19]

DuBois

[11] 4,381,402
[45] Apr. 26, 1983

[54] STEVIOL COMPOUNDS
[75] Inventor: Grant E. DuBois, Palo Alto, Calif.
[73] Assignee: Dynapol, Palo Alto, Calif.
[21] Appl. No.: 331,810
[22] Filed: Dec. 17, 1981

Related U.S. Application Data

[62] Division of Ser. No. 189,243, Sep. 22, 1980, Pat. No. 4,332,830.
[51] Int. Cl.³ .................... C07C 69/753; C07C 69/74
[52] U.S. Cl. .................................. 560/6; 260/503.5; 424/48; 424/49; 426/548; 426/590; 426/658; 536/4.1; 536/18.1
[58] Field of Search ................... 536/4; 260/503.5; 560/6

[56] References Cited

U.S. PATENT DOCUMENTS 3,723,410  3/1978  Persinos .......................... 536/4
4,082,858  4/1978  Morita et al. ..................... 536/4

OTHER PUBLICATIONS

Mosettig et al., "Jour. Amer. Chem. Soc.", vol. 85, 1963, pp. 2305-2309.
Sakamoto et al., "Chem. Abst.", vol. 84, 1976, p. 101729(j).
Kohda et al., vol. 85, 1976, "Chem. Abst.", p. 193026(z).

Primary Examiner—Johnnie R. Brown
Attorney, Agent, or Firm—Burns, Doane, Swecker & Mathis

[57] ABSTRACT

Analogs of the glycoside stevioside are disclosed. These materials have the formula

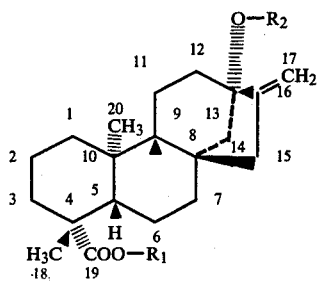

wherein $R_1$ and $R_2$ are as follows:

| $R_1$ | $R_2$ |
|---|---|
| $-(CH_2)_3SO_3^- M^+$ | β-D-Sophorose |
| $-(CH_2)_3SO_3^- M^+$ | $-(CH_2)_3SO_3^- M^+$ |
| $-H$ | $-(CH_2)_3SO_3^- M^+$ | and $M^+$ is a physiologically acceptable alkali metal cation.

2 Claims, No Drawings

STEVIOL COMPOUNDS

This is a division of application Ser. No. 189,243, filed Sept. 22, 1980, now U.S. Pat. No. 4,332,830.

BACKGROUND OF THE INVENTION

1. Field of the Invention

This invention relates to chemical analogs of the sweet glycoside, stevioside, which are themselves sweet and useful as sweeteners.

2. The Prior Art

The leaves of the Paraguayan shrub *Stevia rebaudiana* Bertoni have long been known to be sweet. A sweet crystalline glycoside has been isolated from these leaves. This compound, named Stevioside by the Union International de Chimie in 1921, has been reported to be about 300 times as sweet as sucrose by Bridel et al., *Compt. Rend.*, 192, 1123-5 (1931) and *J. Pharm. Chim.*, 14 (3),99-113; 14 (4),154-161 (1931). Mosettig et al. reported the absolute configuration of stevioside as

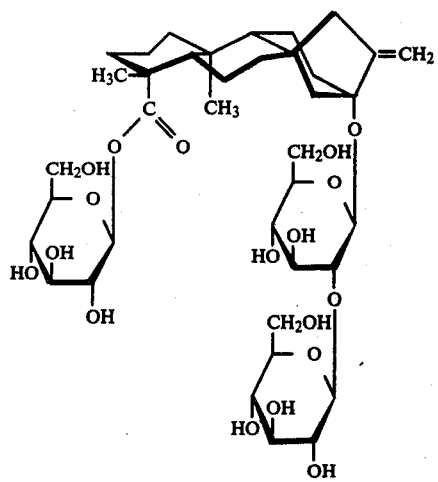

in *J. Am. Chem. Soc.*, 85, 2305-2309 (1963). This material has attracted substantial interest as a potential sweetener. (See Japanese Pat. Nos. 51-52200; 52-47956, 7 and 9; 52-51069; 52-57198 and 9 and 52-62300.) To date, it has not been commercially adopted for two reasons. First, the sweet taste is contaminated with a substantial degree of bitterness (Bridel et al., above). Second, the compound is metabolically unstable. It undergoes enzymatic hydrolysis to the diterpenoid aglycone steviol,

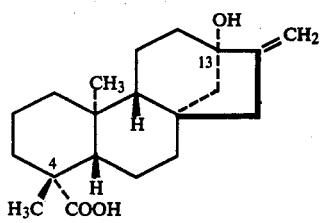

(R. Wingard, J. Dale, J. Brown, R. Hale, *Experientia*, 36, 519, (1980)), a tasteless material that exhibits undesirable physiological activities. Steviol is reported to be a potent inhibitor of ATP synthesis in mitochondria (Vignais, P. U. et al., *Biochim. Biophys. Acta*, 118, 465-483 (1966)) and also shows antiandrogenic effects (Dorfman, R. I., et al., *Endocrinology*, 67, 282-285 (1965).

Reported studies on stevioside have generally focused on its purification and the cultivation of its source. Little has been done to develop or discover analogs which present the desired sweetness without the troublesome disadvantages of bitterness and instability.

STATEMENT OF THE INVENTION

A family of new chemical analogs of stevioside has now been discovered. These materials are useful as sweeteners and unexpectedly have the property of being stable to mammalian gastrointestinal tract conditions and not generating steviol. These compounds have the chemical structures shown in General Formula I.

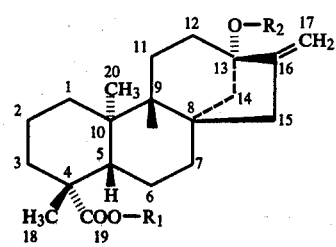

wherein $R_1$ and $R_2$ are as set forth in Table I.

TABLE I

| $R_1$ | $R_2$ |
|---|---|
| $-(CH_2)_3SO_3^- M^+$ | $\beta$-D—Sophorose |
| $-(CH_2)_3SO_3^- M^+$ | $-(CH_2)_3SO_3^- M^+$ |
| $-H$ | $-(CH_2)_3SO_3^- M^+$ | and $M^+$ is a physiologically acceptable alkali metal cation, that is an alkali metal cation such as $K^+$ or $Na^+$ which is accepted as not presenting physiological harm. These compounds are structurally similar to the known compound steviolbioside which is shown by FIG. 1 when $R_1=H$ and $R_2=\beta$-D-Sophorose.

In another aspect, this invention involves the use of these new compounds as sweeteners for comestibles wherein they are admixed with said comestibles.

DETAILED DESCRIPTION OF THE INVENTION

The Compounds

The compounds of this invention may be defined by the structural formula given in General Formula I wherein $R_1$ and $R_2$ are as set forth in Table I. Preferably, $M^+$ is selected from ions of sodium and potassium and more preferably is potassium ion. Most preferably, $R_1$ is $-(CH_2)_3-SO_3^- K^+$ and $R_2$ is $\beta$-D-Sophorose. This most preferred compound can be named as steviolbioside, 3-sulfopropyl ester, potassium salt. The other compounds shown in Formula I and Table I can be named 13,19-bis-O-sulfopropyl steviol, dialkali metal salt, and 13-O-sulfopropyl steviol, alkali metal salt.

Preparation of the Compounds

Steviolbioside, 3-sulfopropyl ester, alkali metal salt may be prepared by saponifying stevioside to steviolbioside with strong base and thereafter reacting the steviolbioside with propane sultone in the presence of alkali metal carbonate.

More particularly, the saponification is carried out by reacting stevioside with a molar excess (at least 5 equivalents) of a strong base, especially aqueous KOH or NaOH and particularly aqueous KOH, at elevated temperatures such as from 50° C. to 150° C., preferably 90°–120° C. for a time adequate to effect essentially complete saponification. The concentration of the base is generally from about 1%wt to about 20%wt. The time required would be in the range of from 0.1 hours to 3 hours and would depend upon the temperature employed. At higher temperatures, say 100°–150° C., times from 0.1 to 1 hour are preferred. At lower temperatures, say 50°–100° C., times from 1 to 3 hours are preferred. An aqueous reaction medium is preferred.

Following saponification, the reaction medium is generally neutralized, such as with mineral acid, and the steviolbioside is recovered. This recovery can be effected by crystallization, brought about by cooling or removal of solvent. The steviolbioside can be purified by recrystallization, thin layer chromatography or a like process at this point. Such a purification is generally performed.

The steviolbioside (preferably recovered) is contacted with 1,3-propane sultone under mildly basic conditions to effect addition of the propane sultone to the steviolbioside. About 1 equivalent of propane sultone is used per equivalent of steviolbioside (preferably 0.9 to 1.1 equivalents). A weak inorganic base, such as an alkali metal carbonate, corresponding to the counterion of the final product, is present in an amount about equal to the equivalents of propane sultone. This reaction is conducted at a low to moderate temperature (0° C. to 30° C., preferably 10°–25° C.) for an extended period such as from 12 to 48 hours. This reaction is carried out in liquid phase in an aprotic reaction medium, such as dimethylformamide, N-methyl pyrollidone, acetone, dimethyl sulfoxide and the like.

Following reaction with propane sultone, and neutralization with acid, the product is recovered such as by evaporation, followed by recrystallization. Other equivalent recovery and purification processes may be employed.

A similar process can be used to produce the compound of Formula I wherein $R_1=R_2=(CH_2)_3SO_3^-M^+$. In this case, steviol is used as the starting material and it is reacted with two equivalents of propane sultone in the presence of two equivalents of alkali metal dimsylate or the like in DMSO. This compound can in turn be converted to the compound of Formula I wherein $R_1=H$ and $R_2=(CH_2)_3SO_3^-M^+$ by saponification under the above described conditions. These preparative conditions are merely representative. Other equivalent routes may be employed if desired.

Stability of Compounds

An important property of these stevioside analogs is their stability and resistance to conversion to steviol at the conditions of the mammalian gastrointestinal tract. This property is demonstrated in vitro by anaerobically incubating the compounds of the invention with fresh rat cecal contents for three days at 37° C. At these conditions, no degradation to steviol occurs to a limit of detection of 0.13%. In direct contrast, as reported in the *Experientia* paper of Wingard, et al., noted above, stevioside itself undergoes essentially quantitative degradation to seriously toxic steviol.

Use of the Compounds

The compounds of this invention are useful as sweeteners for comestibles. In this application, they are simply admixed with the comestible by art-known means in dry form or as solutions, preferably in water. Representative comestibles include beverages such as sodas, coffee, lemonade, wine and the like; edibles such as gelatin desserts, candy, gum, cakes, cereals and the like, personal products such as mouth wash and toothpaste as well as pharmaceuticals such as cough syrups, and flavored pills.

The compounds of this invention are about 125 to 200 times as sweet as sucrose on a weight basis. Accordingly, the amounts to be employed may be determined by factoring usual sucrose use levels by this 125-200 value. Thus, for example, a soft drink might be sweetened by adding 0.05 to 0.15% by weight of the present compounds. Mixtures of these materials alone or with known other sweeteners (sucrose, saccharin or the like) may also be advantageously employed.

The invention will be further described by the following Examples. These are provided solely to illustrate the invention and are not to be construed as limiting its scope.

EXAMPLE I

Preparation of steviolbioside, 3-sulfopropyl ester, potassium salt.

A. Steviolbioside

According to the procedure of H. B. Wood, R. Allerton, H. W. Diehl, and H. G. Fletcher (*J. Org. Chem.* 20, 875–883 (1955)), 771 mg (0.96 mmole) of stevioside was saponified with 25 mls 10% KOH at reflux for 1 hour. After cooling, the reaction mixture was acidified to pH 3 with 10% $H_2SO_4$. After further ice-bath cooling for several hours, filtration yielded a white solid. Recrystallization from methanol yielded 560 mg (91%) of steviolbioside as a white flocculent solid.

B. Steviolbioside, 3-sulfopropyl ester, potassium salt

A mixture of 100 mg (0.156 mmole) steviolbioside, 21 mg (0.172 mmol) 1,3-propane sultone, 24 mg (0.172 mmole) potassium carbonate, and 0.50 ml DMF was stirred vigorously at ambient temperature under an inert atmosphere for 24 hours. TLC analysis (Silica Gel F-254; $CHCl_3$-MeOH-$H_2O$/15-10-2) showed one product (Rf=0.40) and the absence of starting material. The reaction mixture was diluted with 2 ml $H_2O$, acidified with 5% HCl to pH 3 and concentrated to dryness in vacuo. The residue was recrystallized from absolute MeOH to yield 71 mg (57%) of the title compound as a white flocculent solid; mp 204°–6°; IR $\lambda_{max}^{KBr}$ 2.91 (O—H), 5.81 (C=O), 6.02 (C=$CH_2$), 8.5 (S=O), 9.5 (S=O)$\mu$; NMR $\delta_{DMSOd6}^{TMS}$ 0.90, 1.12 (two 3H singlets, $CH_3$), 4.4–5.0 (m, 2H, C=$CH_2$); 5.2–5.35 (m, 2H, O—CH—O)ppm; Anal. Calc. for $C_{35}H_{55}KO_{16}S.H_2O$: C, 51.20; H, 7.00; S, 3.91; Found: C, 51.23; H, 7.03; S, 4.08.

C. Stability Test

Steviolbioside, 3-sulfopropyl ester, potassium salt prepared in Part B. was incubated anaerobically for three days at 37° C. with 5 w% fresh rat cecal contents, at concentrations of 0, 0.5, and 1 mg/ml, and in sterile buffer at 1 mg/ml. After centrifugation, the supernatant fractions were freeze-dried, then extracted with THF. The pellet fractions were also extracted with THF. No steviol was found in the THF extracts by HPLC. In this analysis, the smallest discernible steviol peak was 0.05 μg, equivalent to 0.13 and 0.50 μg steviol per ml original suspension for the pellet and supernatant fractions, respectively, corresponding to 0.03 and 0.13% degradation to steviol in the case of the 1 mg/ml suspensions. These results imply that the steviol sulfopropyl ester bond is highly resistant to bacterial degradation. When this test was run using stevioside, essentially quantitative degradation to steviol was observed.

D. Taste Test

Steviolbioside, 3-sulfopropyl ester, potassium salt prepared in Part B. was dissolved in distilled water at a concentration of 0.2 w% and tasted by a group of volunteers. The solution had a very intense sweet taste. The solution was diluted to 0.05 w% and retasted. It had a sweetness equivalent to 6–10 w% sucrose, depending on the taste tester. The taste was very sucrose-like, having minimal off-flavors.

E. Use in Comestibles

Based on the results of Part D, one can employ the compound of Part B as a sweetener for comestibles. In exemplary uses 0.08% by weight of the compound is dissolved in an unsweetened cola beverage, a like concentration of the compound is added to an unsweetened lemonade and to coffee. In each case, sweetness is imparted. In two other cases, 0.04% by weight is added to coffee along with 0.02% by weight of saccharin and 3% by weight of sucrose, respectively. Again, sweetness is imparted by the compound of Part B.

EXAMPLE II

The preparation of Parts A and B of Example I is repeated with one change. In Part B, in place of potassium carbonate, sodium carbonate is employed. This forms steviolbioside, 3-sulfopropyl ester, sodium salt. When this material is evaluated, as in Parts C, D and E of Example I, it exhibits the same advantageous properties observed with the material of Example I.

EXAMPLE III 13, 19-bis-O-sulfopropyl steviol, dispotassium salt.

A. Steviol (305 mg 1.0 mmole) is dissolved in 40 mls of DMSO together with 2.0 mmoles of potassium dimsylate and 2.0 mmoles of propane sultone and held at 15° C. for 24 hours under an argon atmosphere. The reaction mixture was then worked up by acidifying and stripping off solvent in vacuo. The residue is recrystallized for absolute methanol to yield the title compound.

B. A portion of the title compound is evaluated. Another portion (75 mg) is converted to 13-O-sulfopropyl steviol alkali metal salt. This is accomplished by dissolving the material in 5 mls of 10% KOH and heating to 100°–110° C. for an hour. The reaction product is cooled, acidified to pH 3, and, after chilling, filtered to yield the desired compound as a solid.

What is claimed is:

1. A physiologically acceptable dialkali metal salt of 13,19-bis-O-sulfopropyl steviol.

2. A physiologically acceptable alkali metal salt of 13-O-sulfopropyl steviol.

* * * * *